United States Patent
Freyman et al.

(10) Patent No.: US 10,888,639 B2
(45) Date of Patent: Jan. 12, 2021

(54) DELIVERY CATHETERS FOR IN SITU FORMING FOAMS

(71) Applicant: ARSENAL MEDICAL, INC., Watertown, MA (US)

(72) Inventors: Toby Freyman, Lexington, MA (US); Jennifer Mortensen, Somverville, MA (US); Jeffrey Groom, II, Somerville, MA (US)

(73) Assignee: Arsenal Medical, Inc., Waltham, MA (US)

( * ) Notice: Subject to any disclaimer, the term of this patent is extended or adjusted under 35 U.S.C. 154(b) by 762 days.

(21) Appl. No.: 14/472,816

(22) Filed: Aug. 29, 2014

(65) Prior Publication Data

US 2015/0065951 A1 Mar. 5, 2015

Related U.S. Application Data

(60) Provisional application No. 61/872,102, filed on Aug. 30, 2013.

(51) Int. Cl.
| | | |
|---|---|---|
| *A61L 29/08* | (2006.01) | |
| *A61B 17/12* | (2006.01) | |
| *A61B 17/00* | (2006.01) | |
| *A61B 90/00* | (2016.01) | |

(52) U.S. Cl.
CPC ........ *A61L 29/085* (2013.01); *A61B 17/1219* (2013.01); *A61B 17/12186* (2013.01); *A61B 17/12118* (2013.01); *A61B 17/12195* (2013.01); *A61B 2017/00654* (2013.01); *A61B 2017/00898* (2013.01); *A61B 2017/1205* (2013.01); *A61B 2090/064* (2016.02)

(58) Field of Classification Search
CPC ............. A61L 29/085; A61B 17/12186; A61B 17/1219; A61B 17/12118; A61B 2090/064
USPC ......................................................... 604/82
See application file for complete search history.

(56) References Cited

U.S. PATENT DOCUMENTS

| | | | |
|---|---|---|---|
| 4,451,252 A | 5/1984 | Martin | |
| 6,629,947 B1 * | 10/2003 | Sahatjian | ......... A61B 17/12022 604/11 |
| 2003/0032937 A1 | 2/2003 | Griego et al. | |
| 2004/0068249 A1 | 4/2004 | Kampa et al. | |
| 2005/0096588 A1 | 5/2005 | Hagmann et al. | |
| 2010/0100115 A1 | 4/2010 | Soetermans et al. | |
| 2011/0106054 A1 | 5/2011 | Osborne et al. | |
| 2012/0035471 A1 * | 2/2012 | Lee-Sepsick | ....... A61M 5/1452 600/432 |
| 2012/0265287 A1 | 10/2012 | Sharma et al. | |

FOREIGN PATENT DOCUMENTS

| | | |
|---|---|---|
| EP | 1738694 | 1/2007 |
| WO | 2015031742 A1 | 3/2015 |

* cited by examiner

*Primary Examiner* — Phillip A Gray
(74) *Attorney, Agent, or Firm* — Kacvinsky Daisak Bluni PLLC

(57) ABSTRACT

Delivery catheters for in situ forming foams are provided. The catheters include, in various embodiments, coatings, valves, mixing structures, exit ports and combinations of the same.

8 Claims, 14 Drawing Sheets

DELIVERY CATHETERS FOR IN SITU FORMING FOAMS

CROSS-REFERENCE TO RELATED APPLICATIONS

Figure 1:
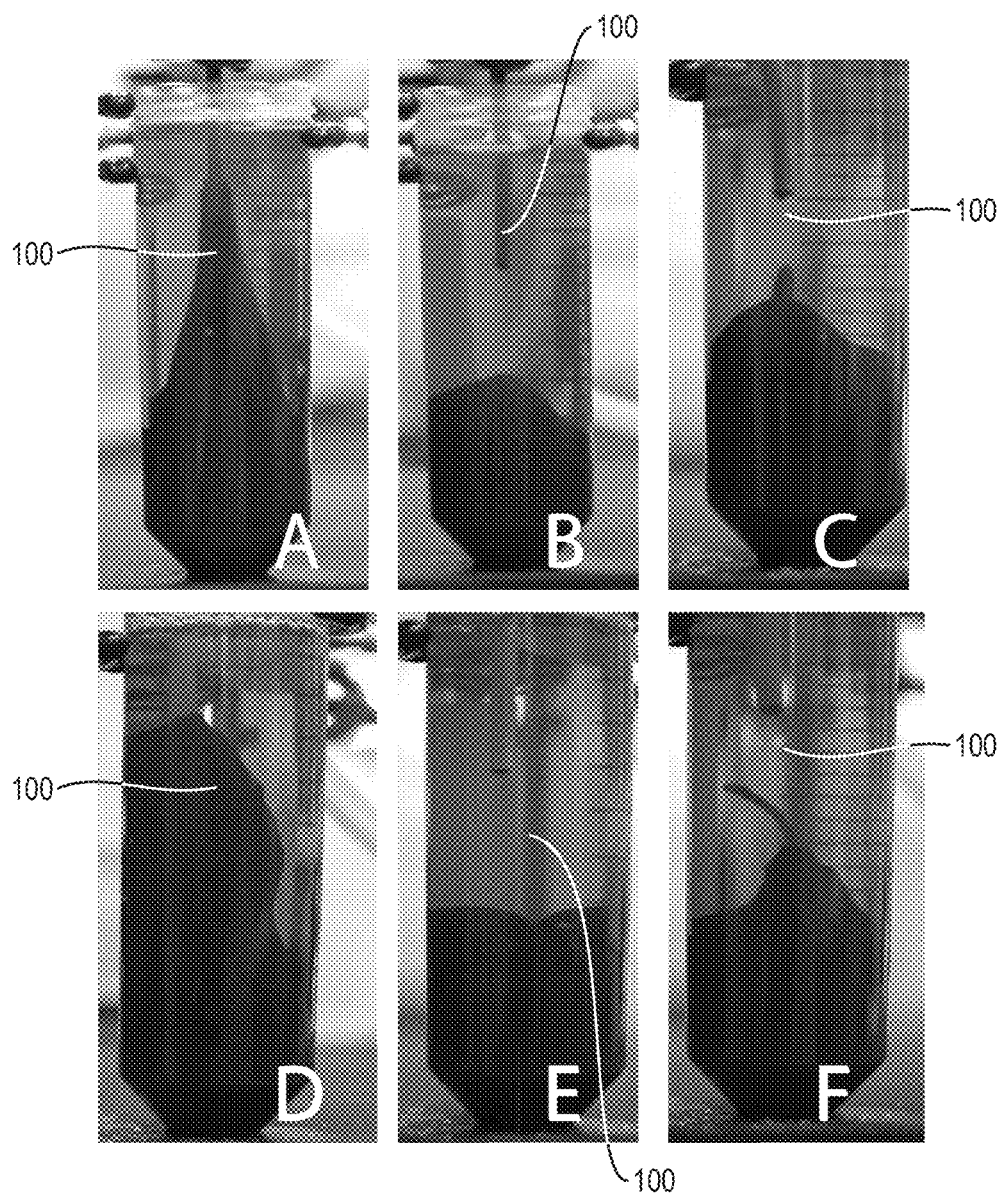

This application claims the benefit of priority to U.S. Provisional Patent Application No. 61/872,102 by Freyman et al, entitled "Delivery Catheters for in situ Forming Foams," and filed Aug. 30, 2013. The entire disclosure of that application is incorporated by reference herein for all purposes.

BACKGROUND

The usefulness of polymer foams in many medical applications is quickly becoming recognized. Among their many advantageous properties, the chemical and physical properties of foams are highly customizable, and their expansile nature permits the relatively non-invasive delivery of small volumes of foaming formulations to spaces within the body, where they can expand to fill the available volume. However, as foam technology has advanced, a need has arisen in the field for systems and methods which deliver in situ foaming formulations with a high degree of temporal, spatial and/or volumetric precision while potentially also performing the mixing, aeration or other functions necessary for proper foam formation in a manner which yields a homogeneous foam product.

SUMMARY OF THE INVENTION

The current invention describes delivery systems and methods for the delivery of a pre-polymer fluid to a space inside the body which then subsequently solidifies, foams, or otherwise becomes immobilized. The foam, once applied, can be used for a variety of clinical applications including stabilizing organs, providing hemostasis and treating endoleaks following endovascular repair of abdominal aortic aneurysms. The foam can also be applied to spaces in the body that are filled with fluid.

In one aspect, the present invention relates to a system for treating a patient which includes a catheter and a formulation that forms a foam when exposed to a water-containing environment. The catheter, has an exterior surface, proximal and distal ends and a lumen (defining an inner surface) which extends between the proximal and distal ends and through which the formulation can be flowed. The catheter also includes a polymer coating on at least one of the exterior and interior surfaces. In various embodiments, the coating is polyvinylalcohol or polyvinylpyrrolidone, the lumen of the catheter includes a valve disposed toward the distal end, which valve opens in response to a pressure above a threshold to allow formulation to flow out. The valve is optionally a duckbill valve. In some cases, where the formulation is hydrophobic, the polymer coating is hydrophilic, while in other cases both the formulation and the coating are hydrophilic. And, in some instances, an opening to the lumen at the distal end of the catheter is non-circular in shape, being instead, for example, a half moon, a slit, and an annulus, while in other instances, the catheter includes a plurality of exit ports within a side wall, and the distal end of the catheter is optionally sealed.

In another aspect, the present invention relates to a system for treating a patient that includes a catheter with proximal and distal ends, first and second lumens, and first and second fluids that react to form a foam when mixed. The first lumen extends from the proximal end of the catheter to its distal end, while the second lumen extends from the proximal end to one or more exit ports some distance away from the distal end of the catheter; the exit port opens into the first lumen, fluidly connecting it to the second lumen. In various embodiments, the exit port or ports are angled relative to the long axis of the catheter so that, when the first and second fluids are flowed through the first and second lumens, one or more jets of the second fluid is formed in the first lumen, or the exit port(s) may be sized, shaped and spaced to form droplets of the second fluid within the first lumen. In other cases, the first lumen includes a mixing structure distal to the exit port(s), which structure can be one of a helical static mixer, an impingement structure, and a plurality of exit holes. If an impingement structure is used, it is optionally stepped, linearly tapered, or parabolically tapered. If a plurality of exit holes are used, the catheter can include a sleeve enveloping the exit holes and directing their outflow into a single direction.

DRAWINGS

In the drawings, like reference characters denote like features of the embodiments of the invention through the different views. Unless otherwise specified, the drawings are not necessarily to scale, with emphasis being placed on illustration of the principles of the invention.

FIG. 1 includes several views of foam deployment using polyvinylalcohol (PVA)-coated and uncoated catheters.

Figure 2:
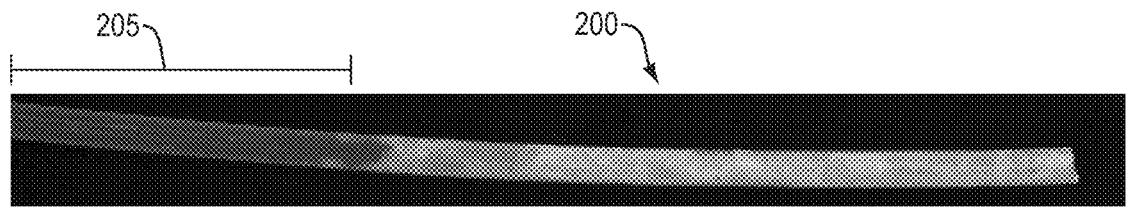

FIG. 2 shows a side view of a catheter having a distal section bearing an exterior polymer coating.

Figure 3:
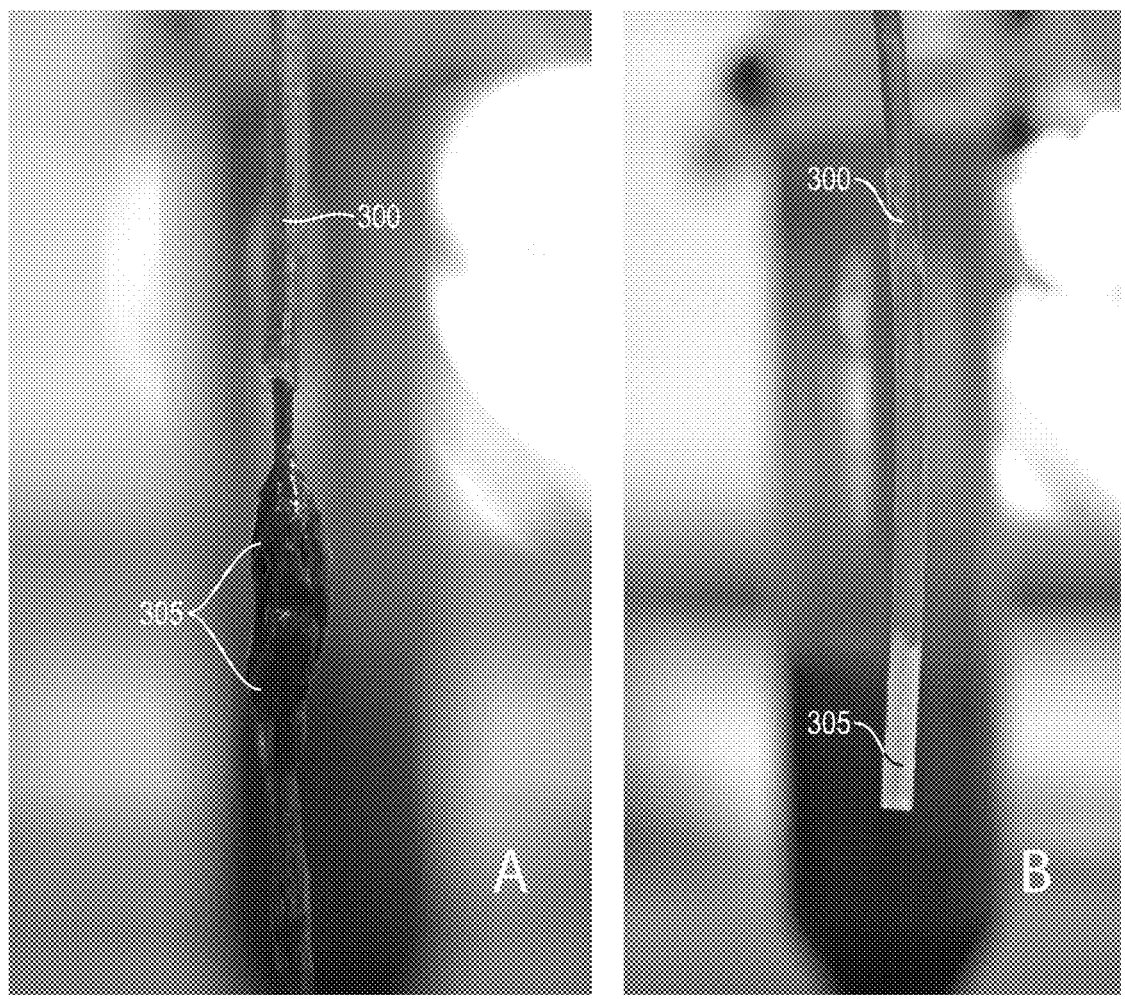

FIG. 3 includes views of a one-part foaming formulation dispensed and retracted through (A) uncoated and (B) coated catheter lumens.

Figure 4:
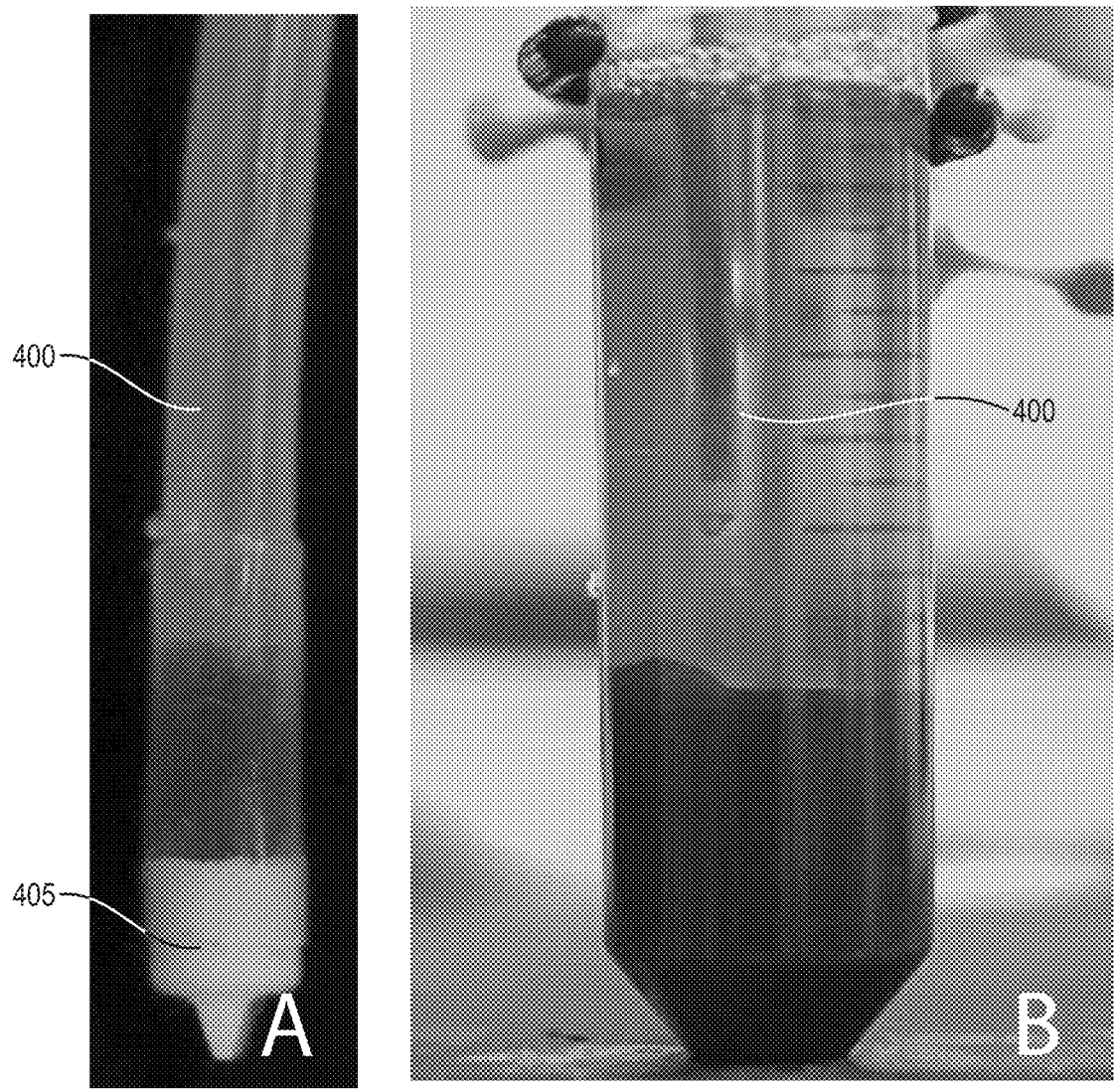

FIG. 4 includes (A) a side view of a foam dispensing catheter with a duckbill valve at its distal end, and (B) the results of dispensing a foaming formulation through the catheter of (A) and then retracting the catheter.

Figure 5:
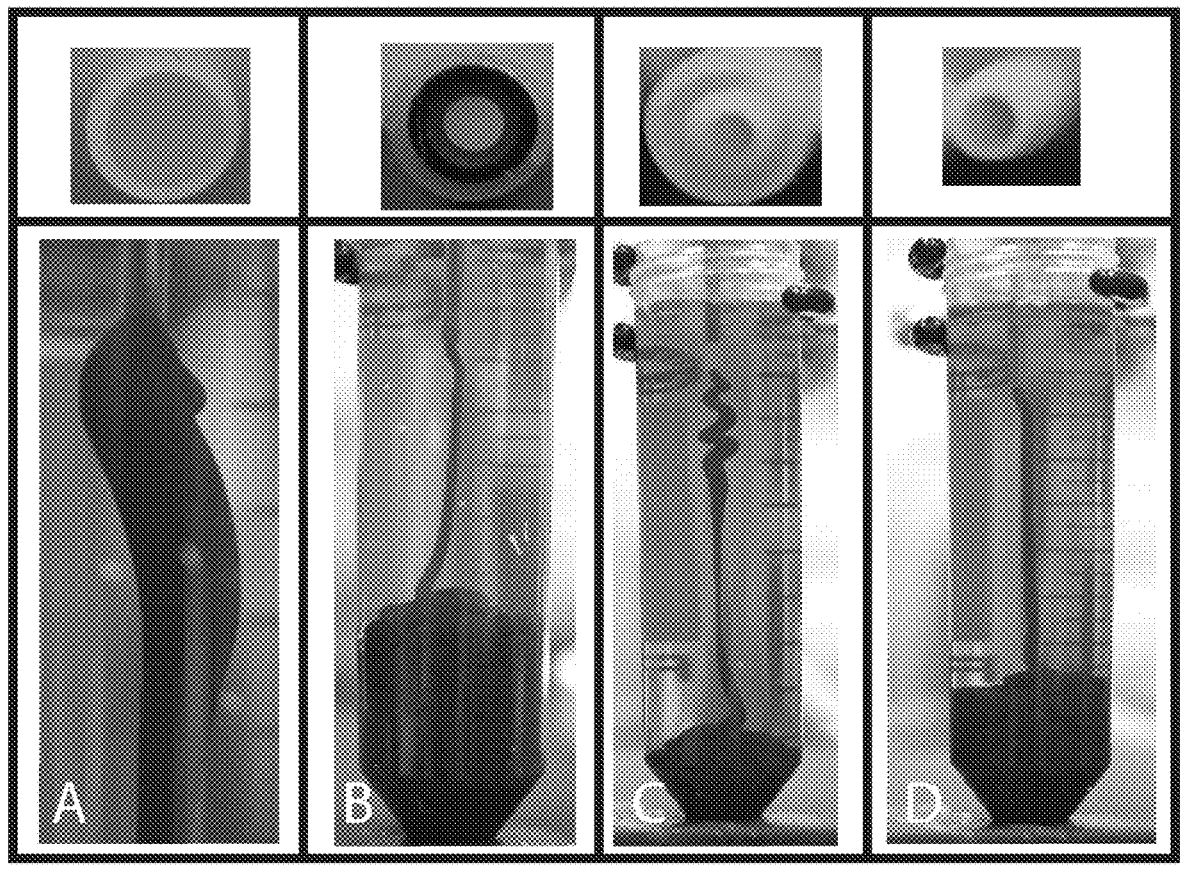

FIG. 5 includes several views of catheters having distal exit ports with irregular or non-circular cross-sectional shapes.

Figure 6:
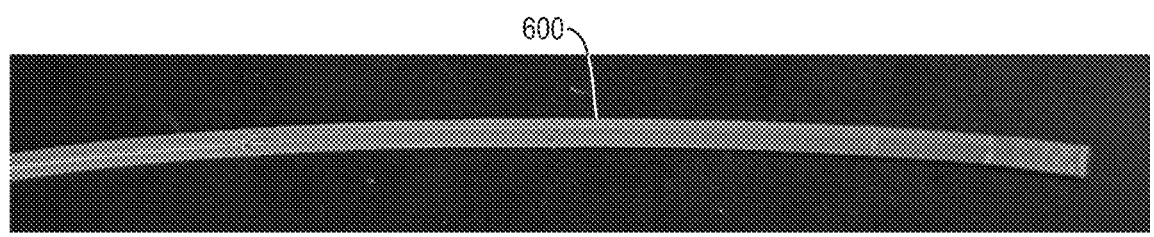

FIG. 6 includes a side view of a catheter including a plurality of side exit ports.

Figure 7:
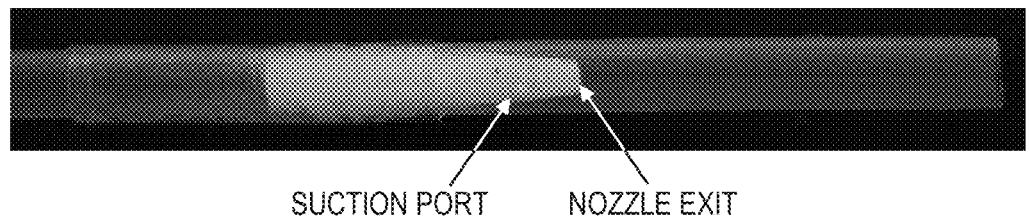

FIG. 7 includes a side view of a catheter configured for mixing ambient fluid into a one-part formulation.

Figure 8:
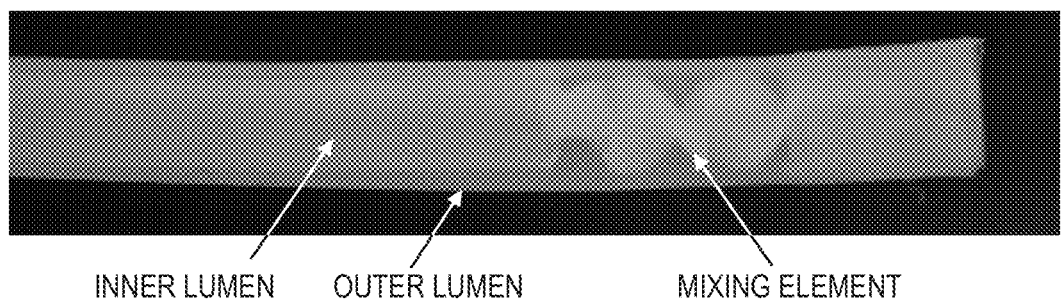

FIG. 8 includes a side view of a catheter including an internal mixing element

Figure 9:
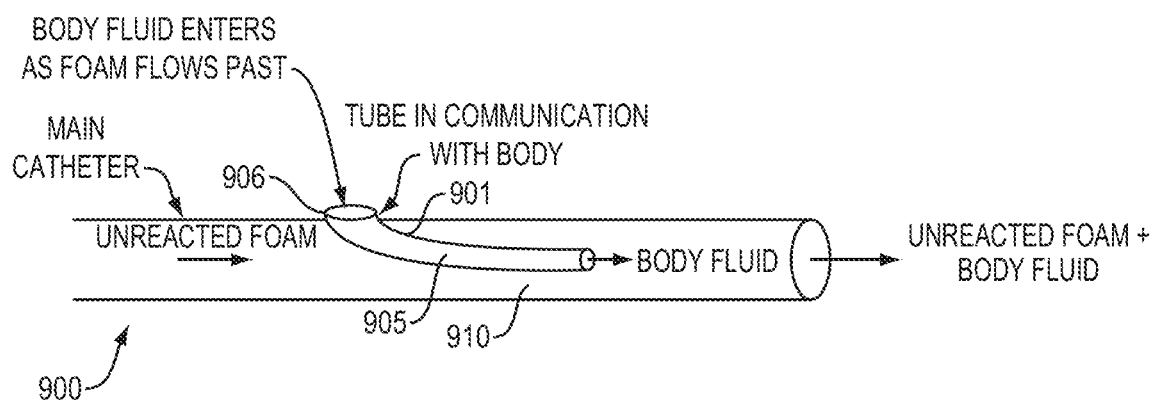

FIG. 9 includes a schematic cross-sectional view of a catheter configured for mixing ambient fluid into a one-part formulation.

Figure 10:
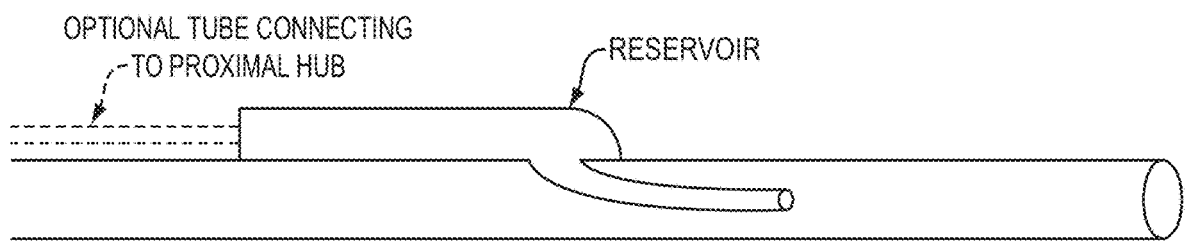

FIG. 10 includes a schematic cross-sectional view of a catheter configured for mixing ambient fluid into a one-part formulation.

Figure 11:
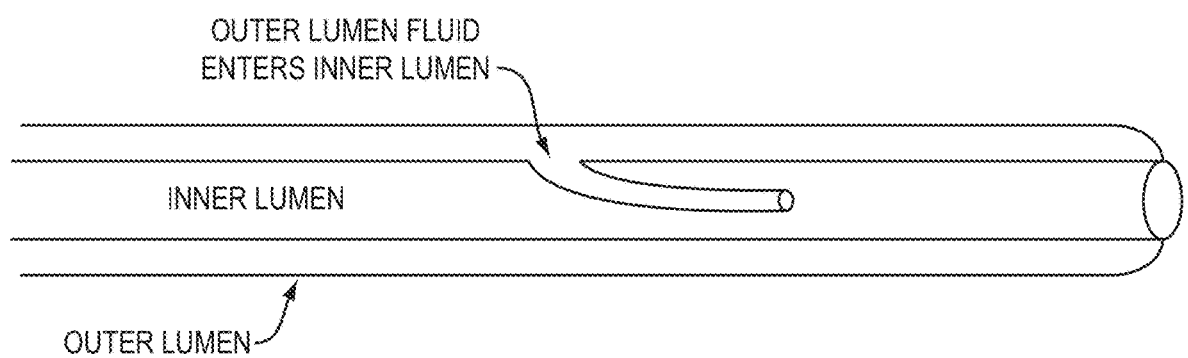

FIG. 11 includes a schematic cross-sectional view of a catheter configured for mixing ambient fluid into a one-part formulation.

Figure 12:
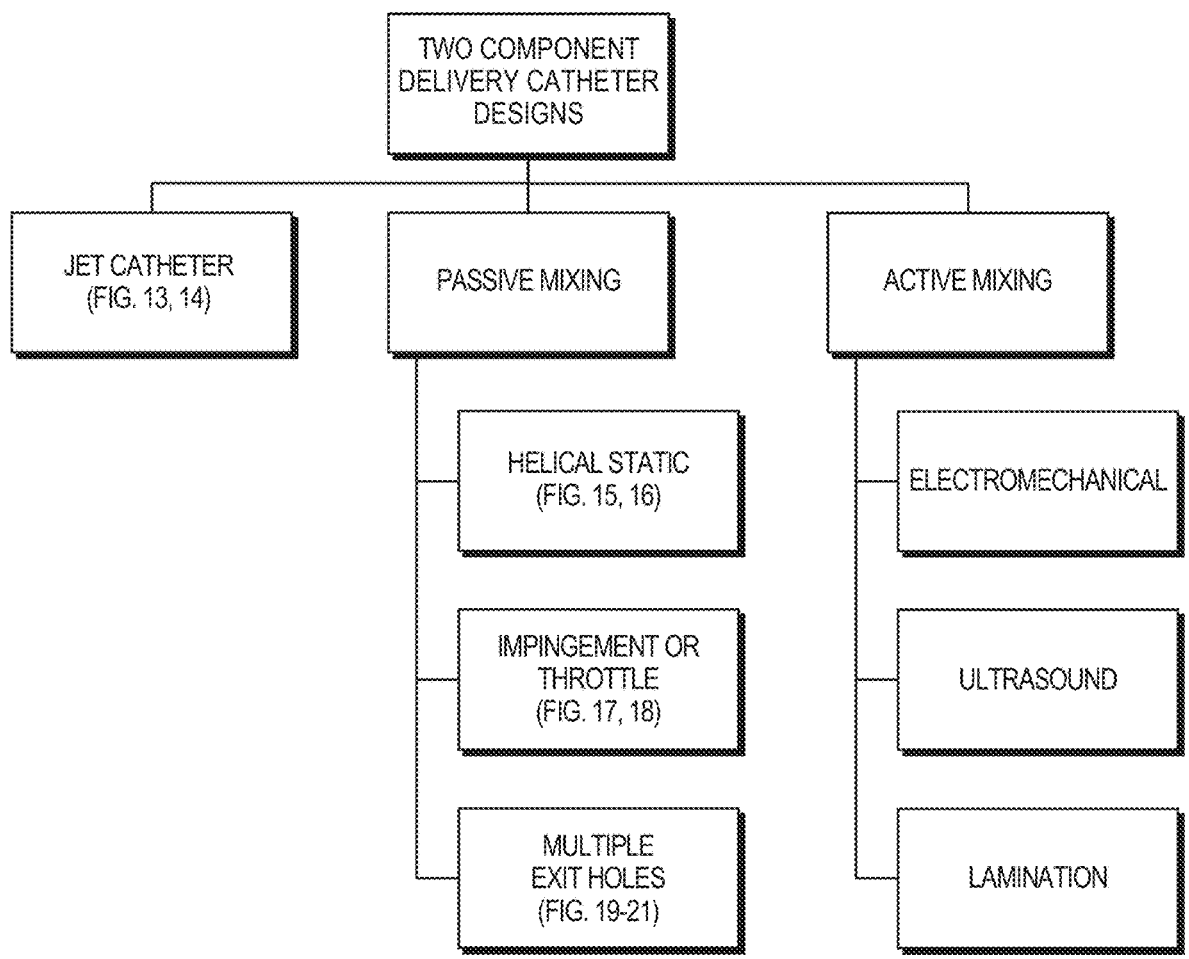

FIG. 12 includes a flow chart representing various two-component mixing and/or delivery catheter designs discussed herein.

Figure 13:
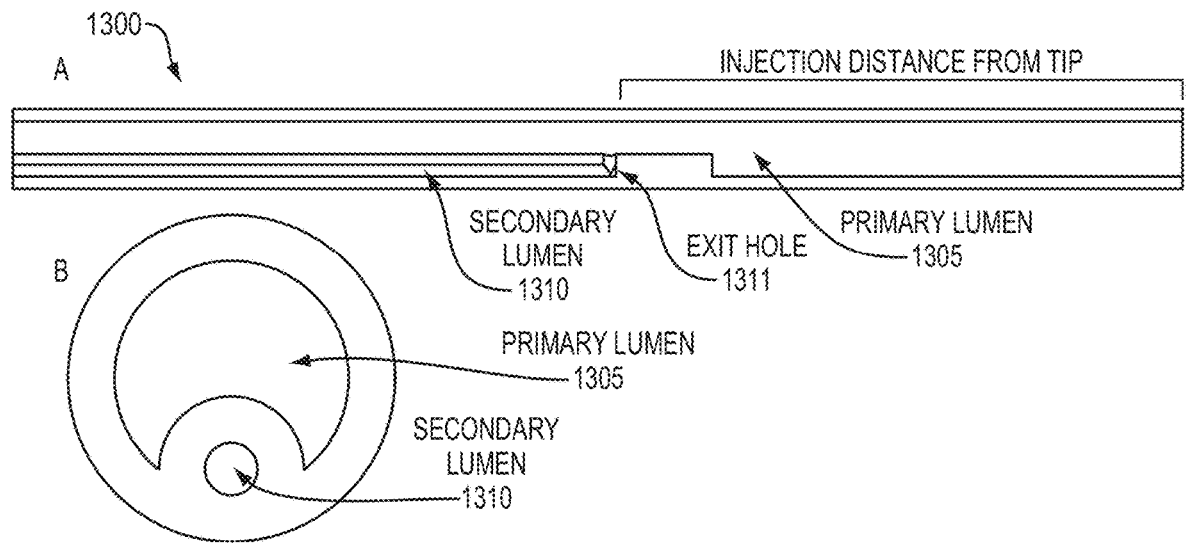

FIG. 13 includes schematic side and transverse cross sectional views of a jet catheter.

Figure 14:
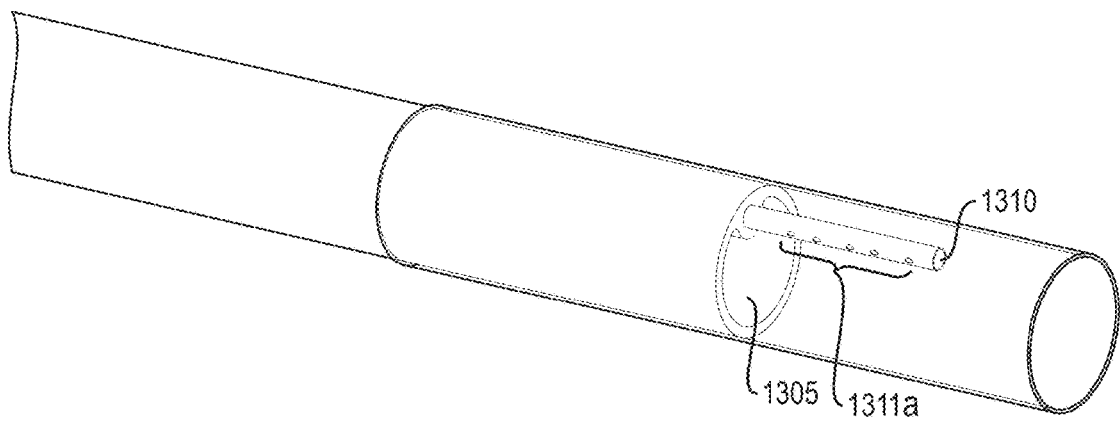

FIG. 14 includes a schematic side view of a droplet-generating catheter.

Figure 15:
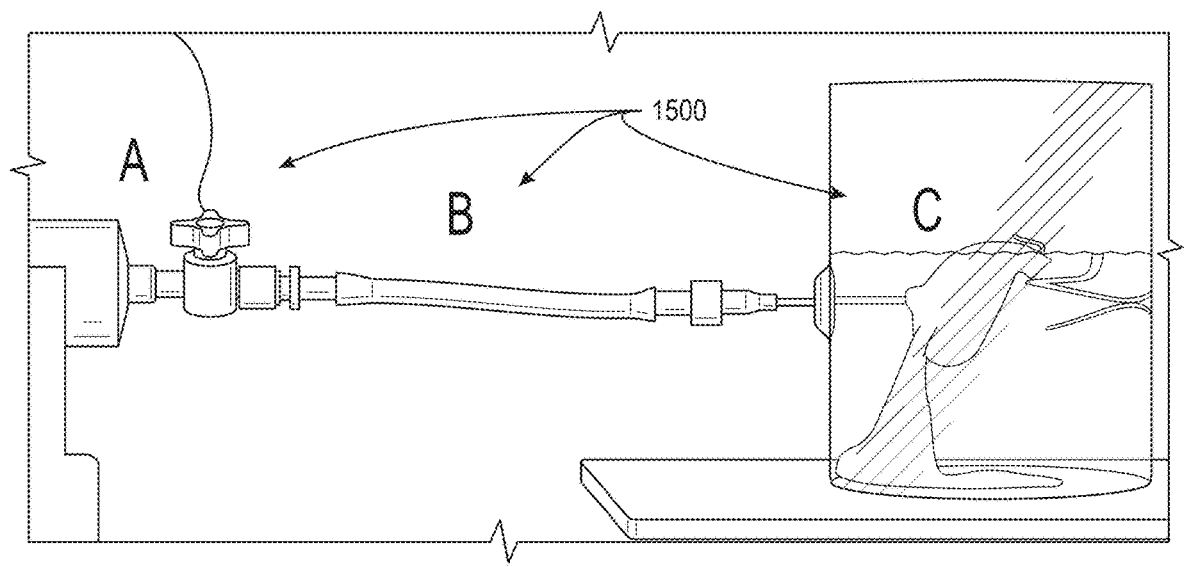

FIG. 15 includes a photograph of a 16-turn helical mixing element.

Figure 16:
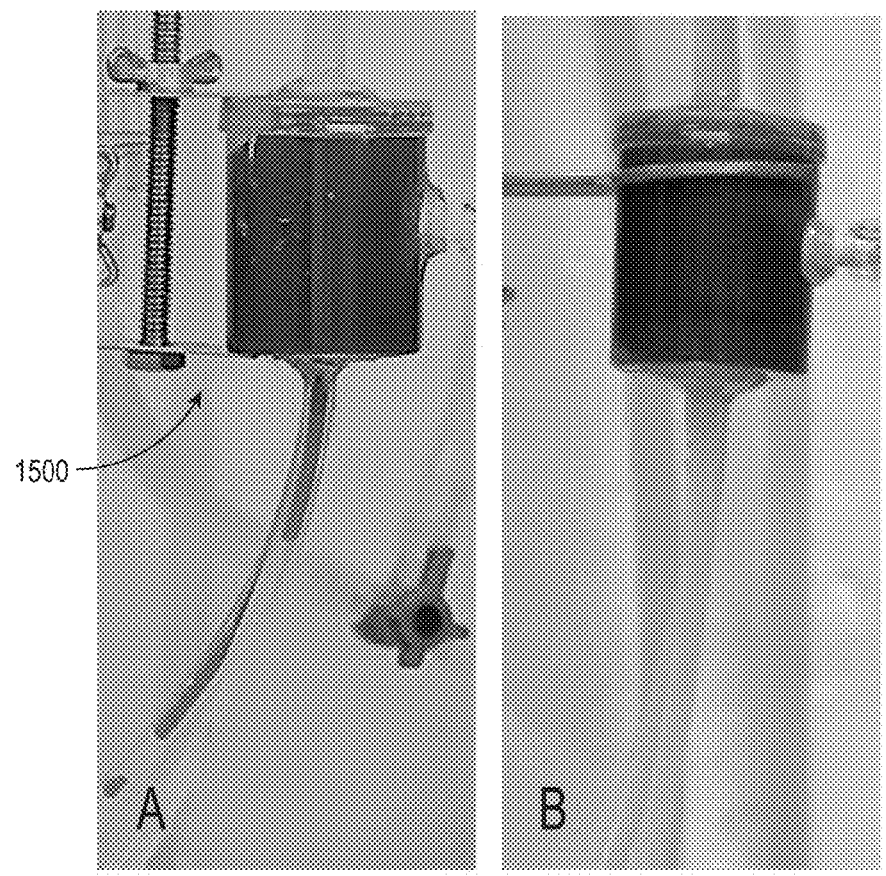

FIG. 16 includes views of experiments testing the migration and curing of (A) unmixed foaming formulation and (B) foaming formulation passed through a 16-turn helical mixing element.

Figure 17:
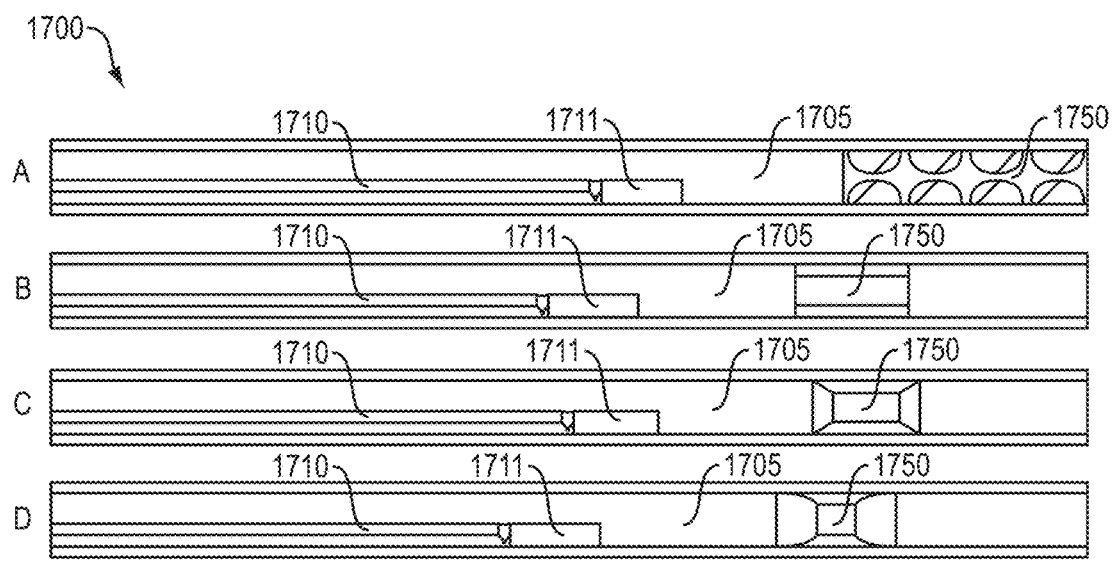

FIG. 17 includes several schematic cross-sectional views of catheters including helical or impingement/throttle mixing elements.

Figure 18:
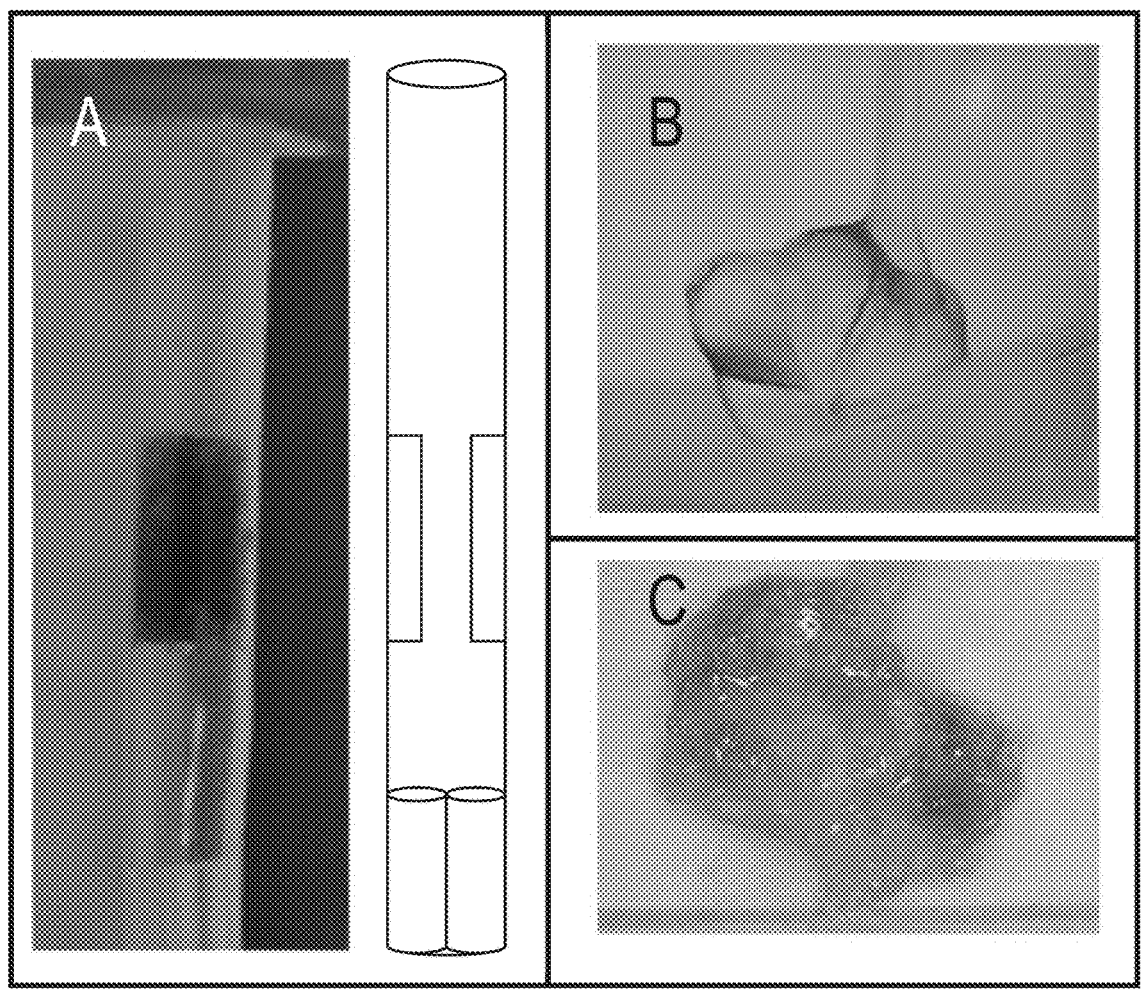

FIG. 18 includes several views of the dispensing of foam components through a catheter having a shouldered impingement mixing element.

Figure 19:
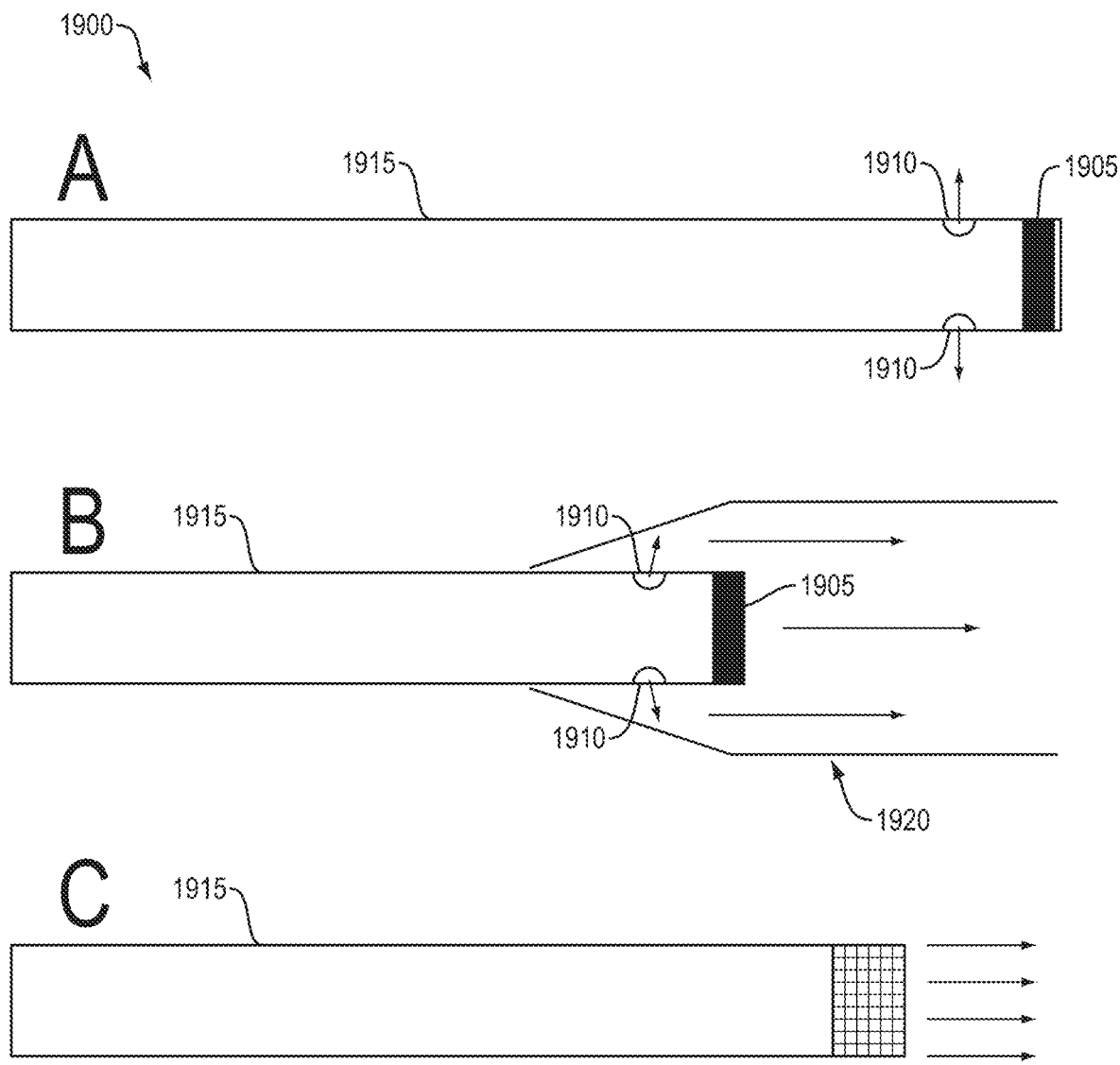

FIG. 19 includes schematic views of various catheter designs incorporating side apertures.

Figure 20:
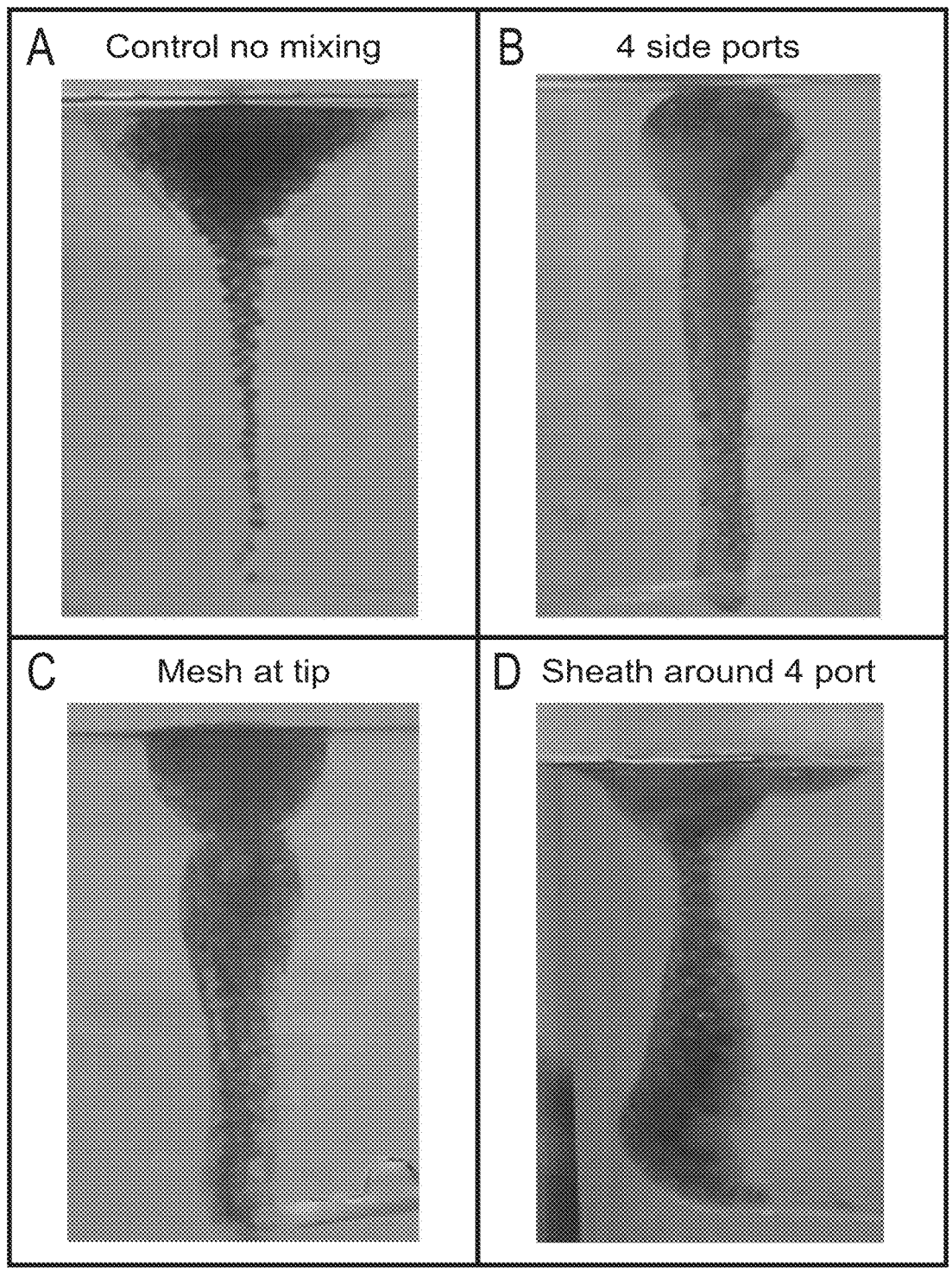

FIG. 20 includes images of foaming formulation component mixing achieved by catheters according to the designs shown in FIG. 19.

Figure 21:
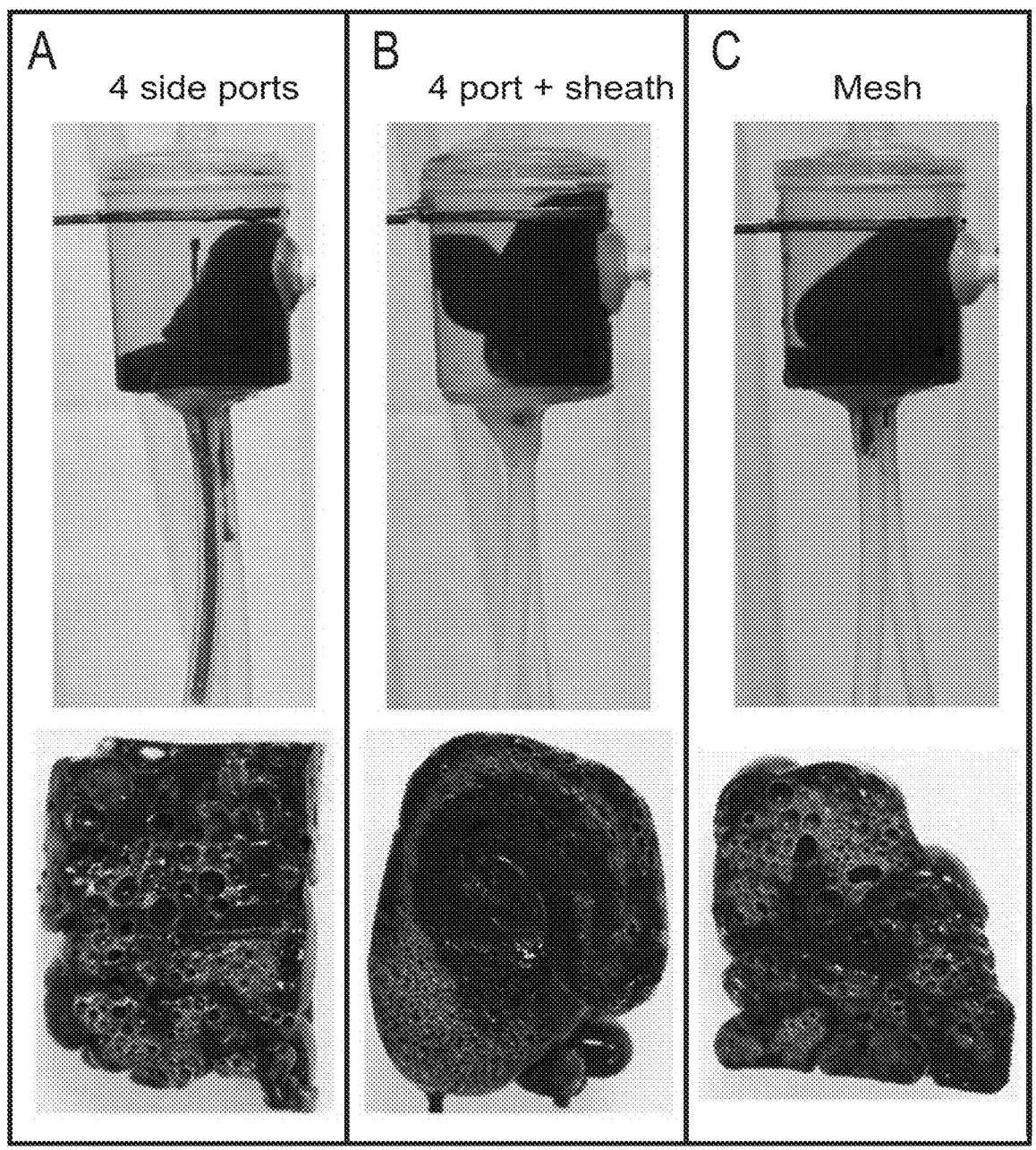

FIG. 21 includes images of foams formed by catheters according to the designs shown in FIG. 19.

Figure 22:
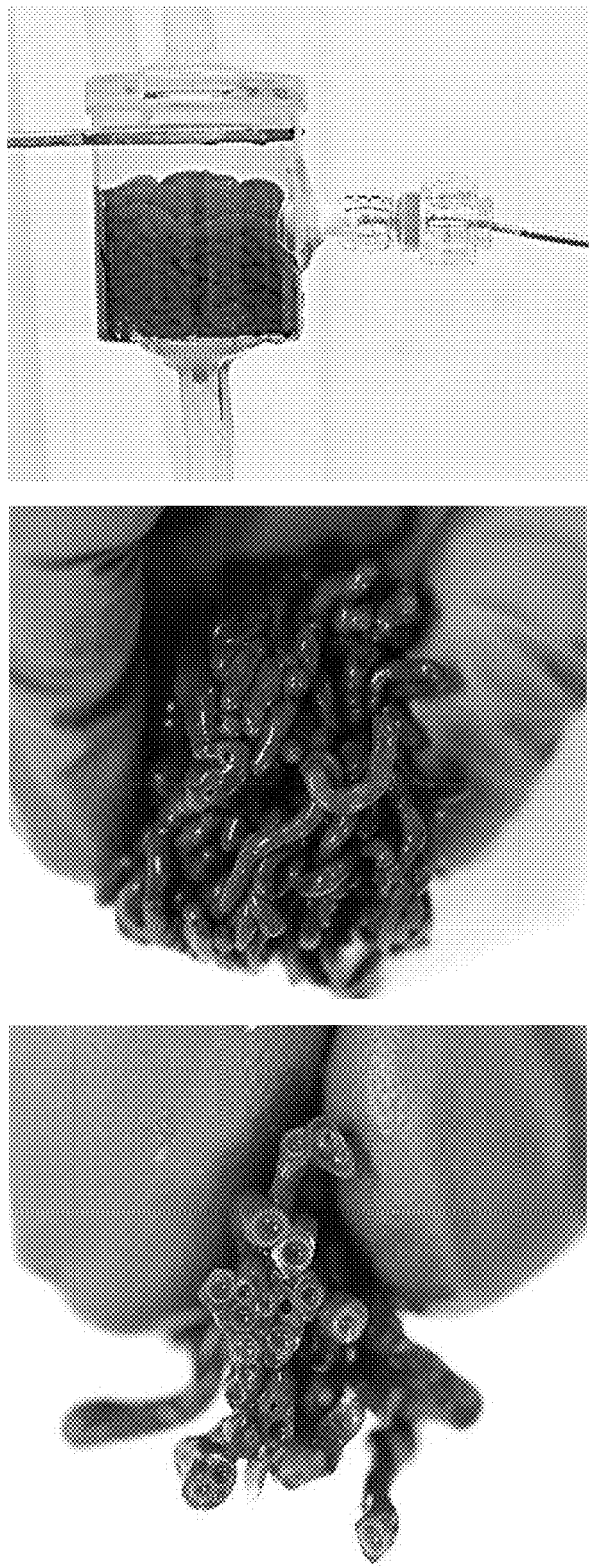

FIG. 22 includes various views of foams formed according to certain embodiments of the present invention.

DETAILED DESCRIPTION OF THE PREFERRED EMBODIMENTS

For the purposes of this disclosure, the terms "formulation," "foam formulation," "pre-polymer," and "pre-polymer formulation" are used interchangeably to designate a polymer-based system or material capable of further reaction in a vessel or cavity. These terms can refer to a single pre-polymer material, or to a pre-polymer material blended with other additives (e.g., catalysts, surfactants, solvents, diluents, crosslinkers, chain extenders, blowing agents, etc.) to create a pre-polymer formulation. The polymeric foams as used herein can include, but are not limited to, any suitable foam formed in situ from a one, two, or multi-part formulation as described U.S. application Ser. No. 13/209,020, filed Aug. 12, 2011 and titled "In situ Forming Hemostatic Foam Implants," U.S. application Ser. No. 12/862,362, filed Aug. 24, 2010 and titled "Systems and Methods Relating to Polymer Foams," each of which are incorporated by reference herein for all purposes.

As used herein, a material is described as a "fluid" if it is flowable, as is the case with, for example, fluid, semi-solid, and viscous materials. As used herein, a material is said to "foam" in that it undergoes a chemical and/or physical change that results in the formation of a foam, a solid, a semi-solid, or a more viscous fluid. A "fluid," as that term is used in this disclosure, can comprise a singular polymer fluid, or can comprise a plurality of polymeric fluids.

In Situ Forming Foams

Generally, in situ foaming formulations used with catheters of the invention are provided as one-part or two-part formulations which react to form a polyurethane foam. A one-part formulation typically consists of an isocyanate-functionalized pre-polymer. This pre-polymer system optionally additionally contains multiple polymer species, catalysts, surfactants, chain extenders, crosslinkers, pore openers, fillers, plasticizers, and diluents. The pre-polymer foams by the interaction between the pre-polymer fluids that are delivered simultaneously or sequentially, or by interaction with an aqueous environment (e.g., blood, water, and/or saline) upon or after delivery. Preferably the blood, water, or saline controls the volume expansion such that foaming will stop when the blood, water, or saline is depleted from the space where the fluid is being deposited. The viscosity of this pre-polymer is preferably less than 5000 cP and more preferably less than 500 cP. Pre-polymers are preferably formed by the reaction of any suitable di- and/or polymeric isocyanates with any suitable polyols. A strict or true pre-polymer may be formed by a stoichiometric 2:1 NCO:OH ratio. A quasi-pre-polymer may be more preferable in which NCO:OH ratios greater than 2:1 are used. Pre-polymers can be designed to foam to a predetermined, maximum volume based on the isocyanate content, hydrophilicity, and catalyst. Additionally, any of the embodiments above may further be formulated to be radiopaque, fluorescent, or otherwise visible by imaging techniques known to those skilled in the art. Radiopacity may be imparted by incorporation of iodinated contrast materials, barium sulfate, metal particles such as tantalum or titanium, etc. The foams formed from the pre-polymer may be bioresorbable or non-absorbable, and will be biocompatible in the intended application.

A two-part foaming formulation generally consists of two fluid components which are stored separately, then mixed and/or aerated and delivered to a site in the body where they react to form a foam. The fluid components typically include separate functionalized molecules which react to form a cross-linked polymer, for instance a polyol-functionalized pre-polymer and an isocyanate crosslinker, and optionally include additives which modify the physical or chemical features of the foam which is generated by the combination of the two components.

Catheter Coatings, Valves and Exit Ports

In the devices and methods of the present invention, polymeric fluids are injected or deposited into the desired location into the body of a patient by use of a catheter delivery system. As used herein, a "catheter" is any device that may be introduced into or adjacent to a patient's body or target location therein, and comprises at least one lumen of any appropriate size, shape or configuration for the movement of fluid therethrough. As used herein, fluids are described as being "injected", "deposited", "delivered" and the like to mean that the fluids are placed via a delivery catheter at a target location within a patient's body using any suitable means. Depending on fluid viscosity, a hand-powered syringe-assist, pneumatic pressure pump, or other device may be used to increase the flow rate and ease of injection. The catheter delivery system is designed to dispense the unreacted in situ foam material at the target site in the appropriate dose. Any means well-known in the art can be used to deploy the catheter to the target site, including but not limited to guide wires, endoscopes, or percutaneous needles. The embodiments of the invention may also include any additional equipment necessary to deliver the foam to the target site, including but not limited to additional catheters, guide wires, needles, positioning equipment, foam component containers, dispensing and metering systems, and introducer sheaths.

When delivering foam to a target site, full and clean release of the foam delivery catheter from the deployed mass of an in situ forming foam is desirable for several reasons. First, excessive force used to remove a catheter stuck in a mass of foam inside a vessel could result in vessel trauma, injury, or rupture. Second, fragments of foam or catheter could be inadvertently released into downstream vessels during removal of the catheter and cause undesired embolization and tissue necrosis. Therefore, in one embodiment of the invention, at least a portion of the outer surface of a delivery catheter is at least partially coated with a material that eliminates the ability of the foam to stick to the catheter, allowing the catheter to be removed cleanly from the foam without significant resistance. As used herein, the foam and/or pre-polymer is said to be "detached", "released", "removed" or the like from the delivery catheter to synonymously mean that the foam and/or pre-polymer is substantially cleanly separated from the delivery catheter. In some embodiments, the coating is a hydrogel or hydrophilic material such as PV A, PVP, PEO, polyurethane, silicone hydro gel, sodium polyacrylate, acrylate polymers and copolymers. Other materials from natural sources for formation of hydrogel coatings include: agarose, methylcellulose, hyaluronan and hyaluronic acid. Any other suitable hydrophilic or otherwise lubricious coatings known in the art may be used.

Referring now to FIG. 1, nonstick coatings applied to interior and/or exterior catheter surfaces can facilitate the application of a foam to a small cavity (simulated here by a 50 mL conical tube) as well as the smooth detachment of the catheter from the foam after it has partially or completely cured. For the examples shown in FIG. 1, the conical tube was filled with serum, the catheter 100 was extended through the tube from the top downward, such that the tip was placed at the bottom of the tube, and the foam was dispensed. As shown in FIG. 1A, when the formulation is delivered using an uncoated PTFE (polytetrafluoroethylene) catheter 100, the dispensed foaming formulation adheres to the tip of the catheter as the catheter is retracted, resulting in the upward displacement of the foam. By contrast, when the PTFE catheter 100 is coated with polyvinylalcohol (PVA) (FIG. 1B) or a polyvinylpyrrolidone (PVP) (FIG. 1C), it separates easily from the formulation. Similar results are obtained when a polyether block amide (sold under the trademark Pebax by Cedex, Paris, France) catheter 100 is used either uncoated (FIG. 1D) coated with PVA (FIG. 1E) or PVP (FIG. 1F).

Any suitable method known in the art for coating catheters may be used, including but not limited to: dip coating, spray coating, chemical or vapor deposition, painting, roll coating and spin coating. Any suitable method known in the art for fixing the coating to the catheter may be used, including but not limited to: drying, vacuum treatment, crosslinking, heat, cold, light, chemical exposure, or dehydration. These steps may be used alone or in combination to provide a robust coating on the surf ace of the catheter. For example, FIG. 2 shows a PTFE catheter 200 in which only a 5 cm distal segment 205 is coated with PVA. To coat the catheter 200, the surface of the distal segment 205 is roughened with an abrasive to increase the surface area available for the coating to adhere to; the distal segment 205 of the catheter 200 is then dip coated in a 5% PVA solution, which is cross-linked by cooling to −20° centigrade. In certain embodiments, the catheter 200 is coated along its entire exterior length, or alternatively along a certain length of the distal tip where foam is most likely to contact the catheter. In some embodiments, the coating is located on at least a portion of the inner surface of the catheter (for instance the interior near the distal tip of the catheter), at least a portion of the outer surface of the catheter, or at least on portions of both. Preferably these catheters are between 1 and 24 French (Fr) and between 20 and 160 cm in length, though any catheter well known in the art may be used. Preferably this coating length extends between 0.05 cm and 100 cm from the distal tip of the catheter. More preferably, this coating length extends between 1 cm and 30 cm from the distal tip of the catheter.

In some cases, interior surfaces of catheters according to the invention are coated with a hydrophilic polymer such as a PVA or PVP. As such, adherence of the pre-polymer and/or foam to the delivery catheter is minimized or eliminated, resulting in such material detaching substantially cleanly from the delivery catheter. This principle is illustrated by the application of negative pressure to the lumen of uncoated and coated catheters 300 as shown in FIG. 3. FIG. 3A shows that, when suction is applied to an uncoated PTFE catheter 300, partially coagulated foaming formulation adheres to the tip 305 of the catheter 300; by contrast, no adhesion is observed when a PVA coating is applied to the distal portion of the lumen.

Some embodiments of the invention provide for a means to assist in or otherwise create a clean separation between the delivery catheter and the foam and/or pre-polymer. One embodiment includes the use of a one-way valve at the tip of the catheter that only allows formulation to flow out of the catheter under positive pressure but closes when pressure is released or negative pressure is applied in the delivery lumen of the catheter. This embodiment aids to prevent blood, water, saline, or other liquid from wicking or otherwise entering the distal end of the catheter and reacting with the pre-polymer liquid prior to its delivery. This valve can be any one-way valve that is known to those knowledgeable in the art, including but not limited to a duckbill, diaphragm, or ball-valve. An example of a catheter 400 incorporating a duckbill valve 405 is shown in FIG. 4A. When duckbill valve 405 is used, the application of positive pressure above a cracking pressure of the valve 405 results in the expulsion of foaming formulation from the catheter 400. When the applied pressure falls below the valve cracking pressure, the valve 405 closes; in some cases, valve closing is facilitated by the application of negative pressure to the catheter 400. This arrangement permits the clean withdrawal of the catheter 400 following dispensing of the foam, as shown in FIG. 4B.

In certain embodiments of the invention, the valve could also be modified to include a snipping feature that allows the valve to forcibly cut away from the foam when in its closed state. This feature forces the components of the valve together and may be activated by the user from the proximal end. In one embodiment, a coaxial sheath slides over the outside of the delivery catheter, pushing the valve closed using cams, levers or other mechanical components. In another embodiment, hydraulics or water pressure are applied through another lumen(s) inside or outside the delivery catheter and provide a higher pressure or shear force on the valve components. In yet another example, a small balloon or other inflatable member at the distal end is inflated inside or outside the delivery catheter, which applies force on the valve components. The balloon or member can be compliant, or non-compliant. If the balloon or member is inflated inside the delivery catheter, it can be sized to fit the catheter. Once the balloon is inflated, it stops the flow of fluid in the outer catheter. These valve features allow for a closed system in which the unreacted foam is isolated within the catheter and can be removed without worry of leakage.

In some embodiments of the invention, suction is applied following completion of foam delivery to facilitate clean detachment of the foam and/or pre-polymer from a delivery catheter. The suction is created by creating a negative pressure (i.e., a vacuum) on the formulation delivery catheter. The vacuum can be created by several different mechanisms including but not limited to a syringe with a spring-loaded plunger retraction activated by a push button or a vacuum tube connected to the catheter hub by a three way stopcock.

In some embodiments of the invention, the delivery catheters of the present invention are designed to influence an in situ forming foam such that it forms a coil, tube, cylinder or other elongated structure. For example, in certain embodiments the catheter is designed so that it has a diameter change at or near the distal tip. While not wishing to be bound by theory, the inventors believe this catheter modification leads to coil formation by increasing the velocity of the unreacted formulation as it exits the catheter tip. In some embodiments, the increase in exit velocity of the foam formulation can be accomplished by narrowing the area in which unreacted foam can exit the catheter preferably by decreasing the inner diameter (ID) at the catheter tip. In other embodiments, other methods such as changing the tip shape to a slit or other shape will work as well. The increase in exit velocity does not allow foam to build up at the delivery catheter tip and thus creates more surface area in which the foam surface can react and form a skin to create a coil. The length of this diameter reduction at the end of the catheter is preferably between 0.1 and 10 cm. More preferably the length of this diameter reduction is between 0.1 and 1 cm. In alternate embodiments, the catheter tip can have a varying diameter reduction compared to the rest of the catheter length. For example, the diameter of the catheter may reduce linearly, from a proximal end of the catheter to the distal tip to form a conical shape if sectioned longitudinally. In other embodiments, diameter reduction variations include: parabolic, hyperbolic, polynomial, logarithmic, part of a golden spiral, or combinations of these shapes. FIG. 5 illustrates how different catheter tips of the invention form different foam shapes. Preferably, the diameter reduction will reduce the cross-sectional area to between 1 and 99% of the main catheter. More preferably, the cross-sectional area will be reduced to between 40% and 95% of the main catheter. In other embodiments, smaller exit fenestrations are created along the side of the catheter to produce multiple streams of coils along the catheter length. FIG. 6 shows an example of a delivery catheter 600 with six exit ports 605 disposed within the sidewall of the catheter 600. The combined cross-sectional area of the exit ports 605 is less than half of the area of the catheter lumen. Without wishing to be bound by any theory, it is believed that the total cross-sectional area of the side ports should be less than the cross-sectional area of the catheter lumen in order to create sufficient resistance to ensure that material exits through all side ports.

Catheter Tips for Mixing Formulations with Reacting Fluids

In yet other embodiments of the invention, delivery catheters are configured to increase the foam formation rate. For example, in one embodiment, a delivery catheter introduces a fluid that increases the reaction rate of the in situ forming foam before it exits the catheter. As used herein, such a reaction rate-increasing fluid is referred to as a "reacting fluid." Any material known in the art may be a reacting fluid used to interact with the foam to increase reaction rate of the foam, including but not limited to blood, plasma, water, saline, or another catalyst. In certain embodiments, foam is exposed to and/or mixed with a reacting fluid within the catheter. While any suitable means may be used to sample the reacting fluid and apply it to the foaming formulation, in one group of preferred embodiments the reacting fluid is drawn into the lumen of a catheter which contains the foaming formulation without requiring any manipulation by a user. For instance, in some cases, the reacting fluid may be drawn into the lumen of the catheter containing foaming formulation by the Venturi effect. FIG. 7 shows a prototype of the Venturi effect catheter, which includes a suction port and a throttle to create an area of low pressure. Fluids from the environment are pulled into the catheter when the area of low pressure is created by the throttle. The nozzle's decreased diameter increases the foam velocity in the catheter and creates a low pressure zone between the nozzle and the outer catheter wall which draws in reacting fluid from the suction port in the outer catheter wall proximal to the nozzle exit. The nozzle and suction port can be placed anywhere along the length of the catheter but preferably near the distal tip. The length of this nozzle is between 0.5 and 50 cm and preferably between 0.5 and 5.0 cm. In some embodiments the diameter reduction can be linear along the length of the nozzle, and in others the catheter tip can have a varying diameter reduction. For example, the diameter reduction variations include but are not limited to: parabolic, hyperbolic, polynomial, logarithmic, part of a golden spiral, or combinations of these shapes. The suction port may allow into the delivery catheter reacting fluids from the environment such as bodily fluids, or may allow in reacting fluids from an outer catheter lumen. In some embodiments the suction port may be a circular opening, and in other embodiments the opening may be any other shape such as a slit, spiral, or a section of porous catheter material. The size scale of the suction port may vary between submicron pores to several millimeters or centimeters in size or length, depending on the velocity of the foam exiting the nozzle, the type of foam exiting the nozzle, the number of suction ports, or any number of other factors. A filter may be incorporated into the suction port to control entry of any material which may not be desirable for the formation of the foam.

In another embodiment of the invention as shown in FIG. 9, the foaming reaction is increased by a side-tube 905 that runs parallel to and within the delivery catheter lumen 910 with an opening 906 connected to the outer wall 901 of the delivery catheter 900 through which reacting fluid flows in from the environment outside the delivery catheter and exits into the delivery catheter. As the unreacted foam moves past the tip of the tube it creates a negative pressure that pulls fluid from the body into the side tube. For water reactive formulations this will increase the speed of the reaction. An increased foaming reaction may also be accomplished by filling, coating, forming, or replacing the tube with a hydrophilic material that wicks water in from the body or body fluids. In another embodiment, the opening of the side-tube or the wick may be connected to another lumen(s) in the delivery catheter or a parallel catheter to introduce reacting fluid. In some embodiments such as the one shown in FIG. 10, the opening of the side-tube or wick may be connected to a reservoir within the catheter, within the proximal delivery system or generally outside the body.

In some embodiments of the invention, the foaming reaction is increased by a coaxial tube contained within the wall of the delivery catheter. The foam material may flow through the inner lumen of the coaxial tube and the reacting fluid may flow through the outer lumen of the delivery catheter, or vice versa, and the lumen sizes can be tailored to deliver a measured amount of reacting fluid to foam material. In some embodiments, the reacting fluid may be injected alongside the formulation but is stored in a separate cartridge and only interacts with the foam material at the tip of the delivery catheter. In other embodiments such as the one shown in FIG. 11, the outer lumen and inner lumen may be connected with a side-tube which runs parallel to and within the inner lumen, wherein the opening of the side-tube is connected to the outer wall of the inner lumen and either foam formulation or reacting fluid flows from the outer lumen into the inner lumen via the side-tube and increases the reaction rate of the foaming. In some embodiments, the coaxial tube has a mixing element which has features designed to promote mixing and turbulent flow of the foam material and reacting fluid. The mixing element can be as long or short as needed and contain any type of mixing element known to those familiar with the fluid mixing field. Preferably the mixing element will contain between 1 and 30 turns and have a length between 0.1 cm and 30 cm from the distal tip of the catheter. The mixing element will preferably have an outer diameter of same, or slightly smaller than the inner diameter of the delivery catheter lumen to ensure proper mixing. An example of such an embodiment is shown in FIG. 8.

In another embodiment of the invention, the foam delivery system includes a pressure sensor on the proximal or distal end or both of the delivery catheter to enable the determination of whether a treatment has been successful or is complete. For example, a catheter with a pressure sensing feature can be introduced into the excluded portion of an endovascularly-repaired abdominal aortic aneurysm (AAA) sac to indicate the end of foam delivery (i.e., when the sac is full of foam). After all of the collateral vessels (e.g., lumbars, IMA, etc.) become blocked with foam, the excluded portion of the AAA sac becomes a closed system and more formulation delivery will result in a pressure increase within the sac. In one embodiment, if the foam formulation is liquid for a sufficient period of time before curing, a fluid filled catheter can be placed in the sac and transmit a pressure signal to a pressure transducer connected to the catheter hub. In another embodiment, a solid-state miniaturized pressure transducer can be placed at the distal tip of the catheter and transmit a signal through a wire along the length of the catheter to the extracorporeal detector. The pressure detecting lumen of the catheter can be the same lumen as that used for delivery, a separate lumen, or a completely separate catheter. In certain embodiments, the user of the delivery system sets a pre-determined pressure level for the space or body cavity where the foam formulation is to be delivered. It is preferable to use a formulation with foaming characteristics such as short rise time or low expansion ratio, so that pressure feedback is rapid and delivery controllable.

Two-Part Formulation Mixing Catheters

Delivery catheters for two-part foaming formulations are also within the scope of the present invention. Two-part foam delivery catheters generally fall into one of three categories, as illustrated in FIG. 12: jet catheters, passive mixing, and active-mixing catheters.

Jet catheters 1300, as shown in FIG. 13-14, generally include primary 1305 and secondary 1310 lumens extending from a proximal end of the catheter 1300. The secondary lumen 1310 is generally smaller than the primary lumen 1305, though the relative sizes of the primary and secondary lumens 1305, 1310 depends on the viscosity, flow rate, and mixing ratio of the two components. The secondary lumen, 1310 terminates in one or more exit holes 1311 that is fluidly connected to the primary lumen 1310. The exit hole(s) 1311 are, in preferred embodiments, angled relative to the long axis of the catheter, which defines the principal direction of flow of the fluid in the primary lumen 1305, to promote mixing of the first and second foaming components; most preferably the exit hole(s) 1311 are perpendicular to the long axis of the catheter. The exit hole(s) 1311 are generally located between 0 and 50 cm from the distal terminus of the catheter, and preferably between 0 and 10 cm. The diameter of the exit hole(s) 1311 will vary depending on the size of the primary lumen 1305, the viscosity of the formulation components, and the ratio of mixing, but will preferably be in the range of 75 and 250 microns. In use flowing first and second foaming components through the primary and secondary lumens 1305, 1310 results in the formation of one or more jets of the second component, which flow into the primary lumen 1305 and into the first component. Without wishing to be bound by any theory, it is believed that these jets disturb the flow of the first component through the primary lumen, promoting mixing of the two components.

The jet catheter design is, in some cases, modified to promote formation of reactant droplets rather than jets of reactant. Without wishing to be bound by any theory, it is believed that the injection of smaller droplets of one fluid component into another fluid component may improve the efficiency of the reaction between the two components by increasing the surface area available for reaction relative to the volume of the components. Droplet generation may be facilitated in catheter designs such as shown in FIG. 13 simply by reducing the flow velocity through the secondary lumen 1310, as well as by tuning the geometry of the primary and secondary lumens 1305, 1310 and the exit hole or holes 1311.

FIG. 14 shows a schematic view of a droplet-generating catheter in which the secondary lumen 1310 includes five exit holes 1311A oriented perpendicularly to the long axis of the catheter. The end of the secondary lumen 1310 is sealed shut (not shown) such that the fluid component is forced out of the exit holes 1311 into the primary lumen 1305.

Turning now to FIG. 15, delivery catheters according to the present invention may utilize passive mixing means to mix multiple formulation components in order to yield a homogeneous foaming mixture; exemplary passive mixing catheter designs may be quite similar to the jet catheter or other designs described above insofar as they permit first and second formulation components to be combined within a single lumen of the catheter. However, passive mixing catheters also generally incorporate a passive mixing element such as the element 1500 shown in FIG. 15. These passive mixing elements are, preferably, designed to promote mixing of laminar fluid flows, as turbulent flows within delivery catheters may not be desirable. The mixing elements may function, generally, by one or more of the following mechanisms: 1) increase dwell time, 2) enhance diffusion coefficient, and 3) increase interfacial areas of fluids. The dwell time can be increased by having the reactant enter into the primary lumen farther from the distal tip, but there are constraints in the catheter system regarding the first two methods for laminar mixing. Preferably the means of mixing would rely on increasing the interfacial areas of the two components by creating shear, which is especially important if the two liquids are immiscible. This can include any laminar mixing technique known to the field but preferably one or a combination of the following: 1) a helical static mixer, 2) an impingement or throttle in the primary lumen, 3) multiple exit holes including side ports or a mesh at the catheter tip.

With specific reference to FIGS. 15 and 16, element 1500 is a 16-turn static mixer which is effective in mixing two fluid components together. Skilled artisans will appreciate that the precise length, diameter, and number of terms will depend on the relative volumes, viscosities and miscibilities of the two foaming components. FIG. 16 shows the results of deployment of a two-part foaming formulation incorporating a colored dye through (A) an unmixed, zero water catheter system, or (B) a catheter which incorporates a 16-turn static mixer. In both systems, the formulation is dispensed from the top of a cylindrical container which container is open at the bottom to a length of plastic tubing. In the unmixed control (FIG. 16A), the dyed composition has flowed into the tubing at the bottom of the container, implying that the foam does not cure fully before the formulation reaches the bottom of the container; by contrast, when the two-part formulation is passed through the 16-turn static mixer, it does not leak into the tubing at the bottom of the container, indicating that it has cured by the time it reaches the bottom of the container; this faster curing will be understood by the skilled artisan to be a likely consequence of the improved mixing of the components of the two-part formulation used in the experiment.

Turning now to FIG. 17, some catheters according to the invention utilize throttle mixing to drive mixing of first and second foaming components; in the embodiment of FIG. 17, the catheter 1700 includes an impingement 1750 located within the primary lumen 1705 and distal to the exit hole(s) 1711 of the secondary lumen 1710. The impingement 1750 is a narrowing of the primary lumen 1705 that helps mix in at least two ways: 1) as flow rate is held constant the velocity of the two components are increased which increases shear, and 2) the secondary lumen 1710 forces the two fluids closer together by increasing the interfacial area contact. The length of the impingement 1750 preferably ranges between 0.1-1 cm in length, and opens up into the original primary lumen 1705 before the formulation and reactant mixture exits the catheter. Preferably there is only one impingement between in the secondary lumen exit port 1711 and the tip of the catheter 1700, but up to 3 impingements 1750 may be utilized to achieve proper mixing. The impingement, in preferred embodiments, narrows the primary lumen by no more than 75%.

FIG. 17 shows several alternative designs a static mixer (17A), a shouldered impingement (17B), a tapered impingement (17C) and a parabolic impingement (17D). FIG. 18 shows the mixing of two fluid foaming components—one clear, one dyed—achieved by a shouldered impingement catheter both during (18B) and after (18C) deployment.

In some embodiments, catheters of the invention incorporate multiple small exit holes, which increase fluid shear relative to a single larger exit hole. While not wishing to be bound by any theory, a laminar mixing mechanism called split and recombine (SAR), which increases the interfacial areas of the two fluids. One example of taking advantage of this mixing mechanism is creating side ports at the distal end of the catheter that forces the two fluids to exit perpendicular to the fluid flow in the catheter therefore splitting the flow. The number of side ports can be between 2-20, but preferentially between 2-6 and can range in size from 0.05-2 mm depending on the size of the catheter and viscosity of the fluids. The total cross-sectional area of the side port must be equal to or preferably less than the cross-section area of the catheter ID. This allows the material to exit all of the side ports. Preferably the side ports are also located in the same plane, radially along the catheter, this allows the material to exit the side ports evenly as the pressure at each side port is even. Side ports may mix some material combination sufficiently but to increase the quality of mixing a sheath can be used around the side port exit to force the split formulation/reactant mixture back together flowing in the same direction, therefore completing SAR. The distance between the side port and the sheath wall should be enough to allow the material to exit, but preferably less than 1 mm. Another similar strategy to achieve SAR mixing is to use a mesh to force the two fluids through multiple holes and then recombine upon exit. This creates a significant amount of shear without increasing the pressure too much. The mesh can be located anywhere between the secondary lumen exit and the catheter tip, but preferably between 0-10 cm from the tip. The mesh can be made of any material metal or plastic, and preferably has an open area greater than 50% which opening sizes ranging from 0.025-1.00 mm, preferably 0.025-0.5 mm and more preferably 0.025-0.25 mm. These three concepts are depicted in FIG. 19 and testing results in FIGS. 20-21.

Turning first to FIG. 19, an exemplary delivery catheter 1900 includes a sealed distal terminus 1905 and two or more relatively small-gauge exit holes 1910 through the side wall 1915 of the catheter 1900. The catheter 1900 also optionally includes a sheath 1920 which extends over the exit holes 1910 to direct the separate outward flows back together. Alternatively or additionally, FIG. 19C illustrates a catheter 1900 which includes a mesh at its distal terminus 1905 to force the two fluids through a plurality of small apertures, but then permits them to recombine immediately after exiting the catheter.

FIG. 20 shows a set of experiments where formulation (clear) and water (blue) are mixed using different catheter designs. Water is injected perpendicular to flow 5 cm from tip of catheter in each case. (A) Control with just water injection and no means of mixing. Notice the large droplets and pooling at surface, evidence of minimum curing or interaction of the materials. (B) Four side ports in the same radial plane of the catheter, each 90 degrees apart. (C) A mesh is located at the exit of the catheter with a 50% open area and approximately 0.25 mm openings. (D) Same 4 side port design as in (A) with a sheath over top. Notice the very small size and uniform distribution of the water droplets in (B), (C), and (D). Also the lack of pooling is evidence of material curing in each case, resulting from better mixing compared to the control.

FIG. 21 shows the results of deployment of foaming formulations through the same catheter designs discussed above into a flowing model and the subsequent solid foams that are formed. In this figure, the foam is dark or black, and water is lighter. (A) Four side ports oriented radial 90 degrees from each other, (B) Same four port design with a sheath over the side ports, (C) a mesh at the catheter tip. All construction is the same as presented in FIGS. 19 and 20. The length of material flow down the simulated vessels is indicative of material cure and therefore mixing of the two fluids. In (A) the average length was 4.5 cm, (B) 0.25 cm, and (C) 0.75 cm.

While the embodiments above have focused on passive or static mixing mechanisms, embodiments utilizing active mixing means are also within the scope of the present invention. The term "active" in this context refers to the application of external energy to the fluid components to drive mixing. In preferred embodiments, the energy is either electromechanical or ultrasonic in nature. In the electromechanical situation a small electric motor could be hooked up to a drive shaft that extends the length of the catheter. At the end of the drive shaft could be any tip that when rotated would create shearing of the two fluids, but preferably an impeller/propeller or a hoop. The tip could be placed anywhere in the primary lumen between the exit of the secondary/reactant lumen and the distal tip of the catheter. The rotating tip would have to be smaller than the ID of the primary lumen. The tip of the drive shaft could also be placed just outside the catheter, past the distal tip of the catheter. The advantage of placing the rotating tip outside of the catheter lumen would be to reduce the effects of the curing when the two fluids are mixed, keeping the lumen of the catheter clear. Curing the material too fast inside of the catheter lumen could create increased pressure and potential clogging. In one embodiment, a battery would be the preferred power source and the speed of the motor could be controlled through the use of a dial to induce more or less mixing.

Another embodiment of the active mixing catheter involves the use of ultrasonic vibrations to induce shear and therefor mixing of the two components. In this embodiment an ultrasonic probe would run along the length of the catheter and have a tip that ends in the primary lumen of the catheter between the secondary lumen exit and the distal end of the catheter. A power source, preferably a battery, would be used to cause a piezoelectric membrane to vibrate at ultrasonic frequencies. This vibration causes cavitation which in effect causes very high localized shearing to mixing the two components in a small space. This is a common method used in the creation of emulsions. The use of ultrasonic vibrations could also be used at the proximal end of the secondary lumen, before the reactant enters the catheter. The vibrations would cause a pressure wave to propagate through the reactant fluid until the exit. The pressure waves at the exit as the reactant fluid enters into the primary lumen would cause shearing at this interface resulting in mixing. This is a method that has been successful on a microfluidics level. In this case the vibrations are preferable in the ultrasonic range, but could also be at a lower level depending on the viscosity of the fluids and levels of mixing required.

Another embodiment relies on a laminar fluid mixing method called lamination. As before there are two lumens, where the secondary lumen exits into the primary lumen before the catheter exit at the distal tip. The distance from the tip of the catheter where the secondary lumen exits has the greatest influence on the amount of mixing. To laminate the two fluids a pump and valve system would be used to alternate the flow of the fluids to be mixed in the primary and secondary lumens. This creates lamination of the two fluids, and the amount of each fluid injected per segment would be dictated by the mixing ratio of the two fluids. The mixing occurs in this situation because the flow in the catheter is laminar, and with laminar flow the fluids travel as a parabolic flow field with the vertex at the center of the lumen with flow approaching zero at the catheter walls. Because of this property the alternating fluids stretch into each other causing a rapid increase in interfacial areas.

Finally, regardless of the mixing means utilized, it may be desirable in some cases to generate droplets of a uniform size inasmuch as such uniform droplets may contribute to more uniform or homogeneous foams, which may be well suited to some applications. In particular, the degree of homogeneity of a foam could impact its mechanical properties as well as the consistency and reproducibility of specific foam properties.

One way of forming consistent size and spacing of droplets within the formulation stream exiting a catheter is to form coils by increasing the exit velocity of the stream as shown in FIG. 22. The exit velocity of the stream can be increased by reducing the diameter at the very distal tip of the catheter. The length of the diameter reduction should be minimized to prevent undue backpressure on the injection end of the catheter. The length of the diameter reduction is preferably less than 1 cm although other lengths outside of this range can be effective. Another way of improving droplet uniformity within the foam is to match the liquid densities of the reactant and formulation. This will help eliminate phase separation due to buoyancy as the liquid components are curing and reacting into a foam. In yet another way, surfactant is added to the reactant or formulation phase to promote stabilization of the two phases. This can be especially helpful if the reactant and formulation phases are immiscible.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

What is claimed is:

1. A system for treating a patient, the system comprising:
(1) a catheter having proximal and distal ends and having an outer catheter wall surrounding a first and second lumen along the entire length of the first and second lumen, said first lumen extending from the proximal end of the catheter to the distal end and the second lumen parallel to the first lumen and extending from the proximal end of the catheter and terminating in at least one exit port separated by a first distance from the distal end of the catheter and physically separated from the first lumen, the at least one exit port fluidly connecting the first lumen to the second lumen within the catheter; and
(2) first and second fluids configured to form a homogeneous polymeric formulation within the first lumen of the catheter, and to foam when mixed; and
wherein the first lumen includes a mixing structure located distally relative to the at least one exit port, wherein said at least one exit port is located 0 to 10 cm from the distal end of the catheters and wherein the second lumen includes a plurality of exit ports oriented perpendicularly to the long axis of the catheter and wherein the distal end of the second lumen is sealed shut.

2. The system of claim 1, wherein the at least one exit port is sized such that, when the first and second fluids are flowed through the first and second lumens, respectively, a plurality of droplets of the second fluid are formed within the first lumen.

3. The system of claim 1, wherein the mixing structure is selected from the group consisting of a helical static mixer, an impingement structure, and a plurality of exit holes.

4. The system of claim 1, wherein the mixing structure is an impingement structure that is stepped, linearly tapered, or parabolically tapered.

5. The system of claim 1, wherein the first and second fluids comprise functionalized molecules which react to form a cross-linked polymer when mixed.

6. The system of claim 1, wherein the liquid densities of the first and second fluids are consistent with the density of the formulation.

7. The system of claim 1, wherein flow of the second fluid through the catheter produces droplets at the at least one exit port and wherein the size and spacing of the droplets are regulated by a reduction in diameter of the catheter at the distal end of the catheter.

8. A system for treating a patient, the system comprising:
(1) a catheter having proximal and distal ends and having an outer catheter wall surrounding a first lumen extending from the proximal end of the catheter to the distal end and a second lumen parallel to the first lumen and extending from the proximal end of the catheter and terminating in at least one exit port separated by a first distance from the distal end of the catheter, the at least one exit port fluidly connecting the first lumen to the second lumen within the catheter; and
(2) first and second fluids configured to form a homogeneous polymeric formulation within the catheter, and to foam when mixed;
wherein the first lumen includes a mixing structure located distally relative to the at least one exit port and
wherein the second lumen includes a plurality of exit ports oriented perpendicularly to the long axis of the catheter and wherein the distal end of the second lumen is sealed shut.

\* \* \* \* \*